(12) United States Patent
Ray et al.

(10) Patent No.: US 7,721,739 B2
(45) Date of Patent: *May 25, 2010

(54) APPARATUS AND METHOD FOR PREVENTING FLUID TRANSFER BETWEEN AN OVIDUCT AND A UTERINE CAVITY

(76) Inventors: Terry L. Ray, 1118 E. San Angelo, Gilbert, AZ (US) 85234; James W. Zeluff, 11165 Sandy Grove Ave., Las Vegas, NV (US) 89144

( * ) Notice: Subject to any disclaimer, the term of this patent is extended or adjusted under 35 U.S.C. 154(b) by 0 days.

This patent is subject to a terminal disclaimer.

(21) Appl. No.: 11/838,080

(22) Filed: Aug. 13, 2007

(65) Prior Publication Data

US 2007/0272252 A1    Nov. 29, 2007

Related U.S. Application Data

(62) Division of application No. 10/648,078, filed on Aug. 26, 2003, now Pat. No. 7,258,121.

(51) Int. Cl.
*A61F 6/06* (2006.01)
*A61B 17/00* (2006.01)
*A61M 29/00* (2006.01)

(52) U.S. Cl. .................. 128/830; 128/831; 128/838; 128/887; 606/193

(58) Field of Classification Search .................. 128/830, 128/831, 832, 838, 846, 839, 841, 887, 898; 600/29, 32; 606/193, 197, 198
See application file for complete search history.

(56) References Cited

U.S. PATENT DOCUMENTS

| 6,125,850 | A   | * | 10/2000 | Sokal et al. | .................. 128/830 |
| 6,371,118 | B1  | * | 4/2002  | Ray et al.   | .................. 128/830 |
| RE39,533  | E   | * | 3/2007  | Ranoux       | .................. 600/34  |

FOREIGN PATENT DOCUMENTS

GB        2211095 A  *  6/1989

* cited by examiner

*Primary Examiner*—Patricia M Bianco
*Assistant Examiner*—Ophelia Hawthorne
(74) *Attorney, Agent, or Firm*—Parsons & Goltry; Robert A. Parsons; Michael W. Goltry

(57) ABSTRACT

Apparatus for preventing fluid transfer through an opening connecting an oviduct to a uterine cavity includes a body having a base with a periphery and a seal carried by the body for overlying and engaging uterine tissue leading to the opening. The seal receives fibroblast in-growth to create a hermetic seal between the oviduct and the uterine cavity. A peripheral anchor portion extends from the base for securing the body to the uterine tissue leading to the opening, the base overlying the opening.

9 Claims, 3 Drawing Sheets

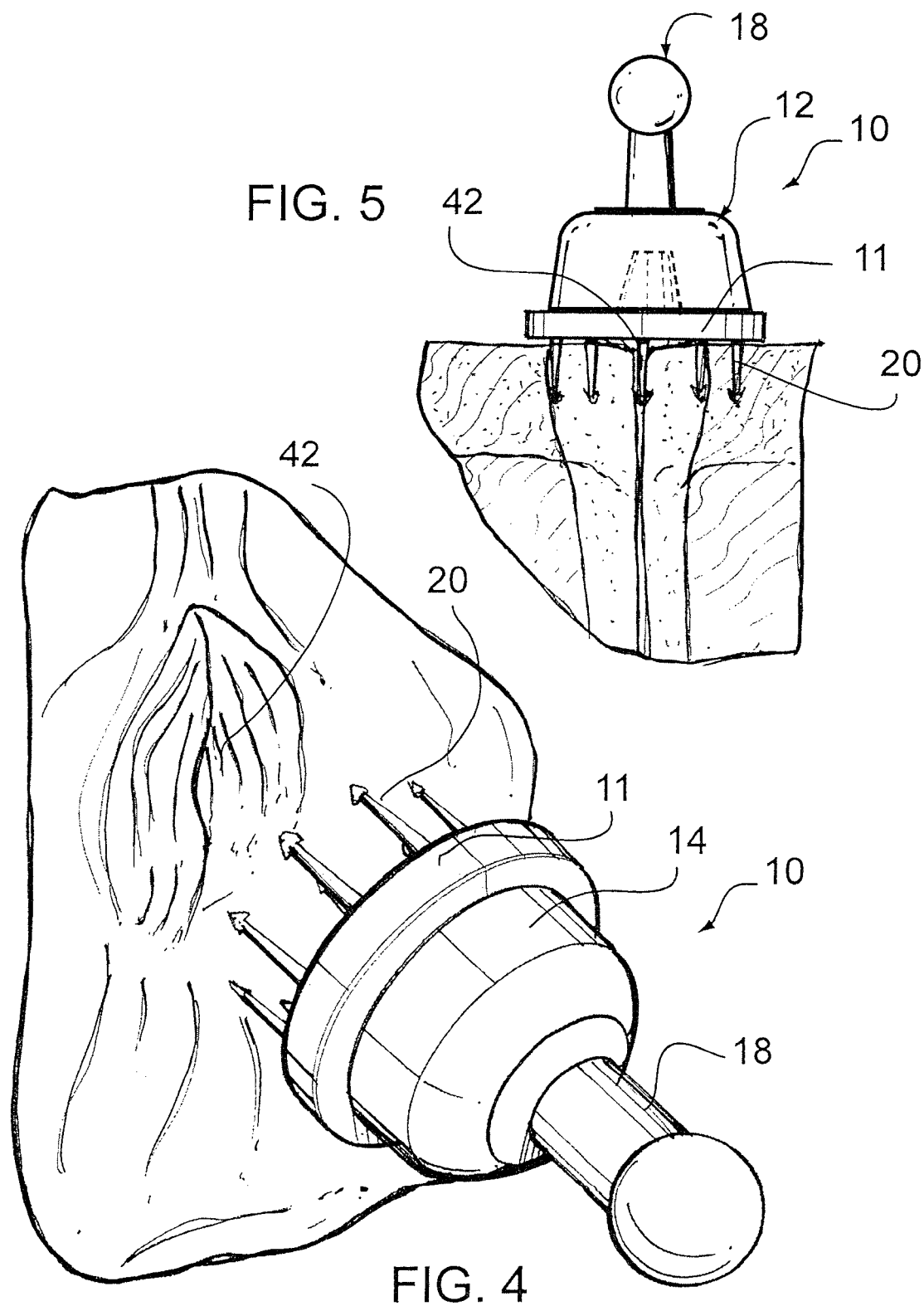

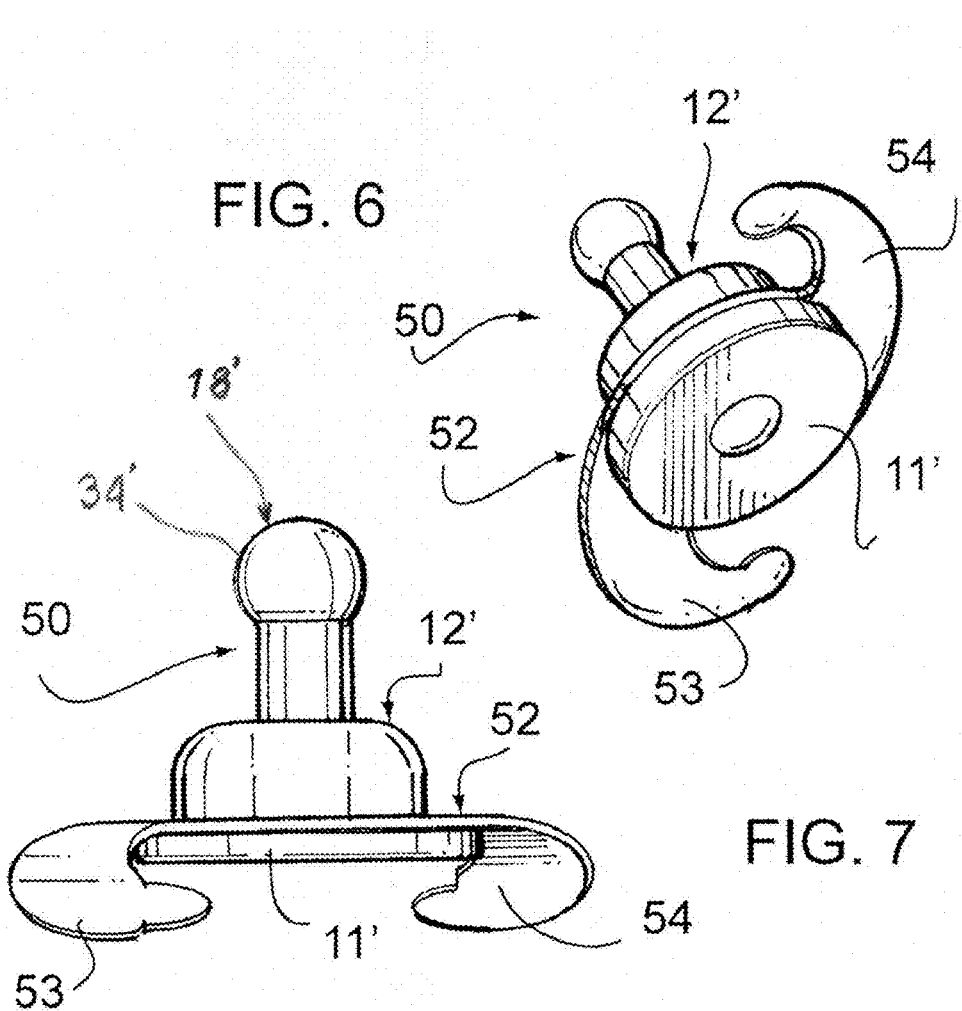
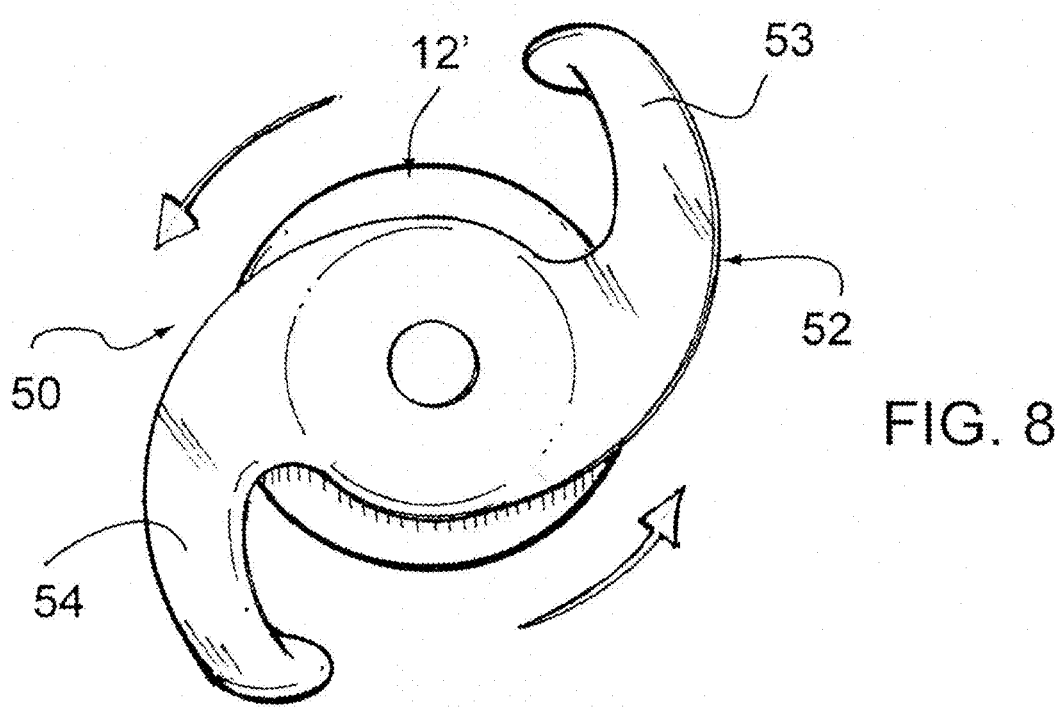

APPARATUS AND METHOD FOR PREVENTING FLUID TRANSFER BETWEEN AN OVIDUCT AND A UTERINE CAVITY

CROSS-REFERENCE TO RELATED APPLICATIONS

This application is a divisional application of currently U.S. application Ser. No. 10/648,078, filed 26 Aug. 2003 now U.S. Pat. No. 7,258,121.

FIELD OF THE INVENTION

This invention concerns birth control and, more particularly, apparatus and methods for preventing fluid from passing into an oviduct of a female reproductive system.

BACKGROUND OF THE INVENTION

In certain circumstances, birth control can be very important, and as such, great effort and research has been expended in this area. There are two primary areas of birth control for female use, other than surgery, including pharmaceutical, and mechanical approaches. Prescription birth control drugs are frequently used, but are expensive and can have adverse physical or mental side effects. Additionally, missing a dosage can have significant effects on the reliability of the treatment. To avoid these problems, many women rely on less expensive mechanical devices as a means for inhibiting conception.

Nearly all mechanical birth control devices and techniques attempt to block fluid transfer between either the vagina and the uterus or the oviducts and the uterus. By preventing fluid transfer between the uterus and the vagina and/or the oviducts, conception is prevented or at least minimized. Although existing mechanical devices and techniques prove adequate, they are often unreliable and difficult to construct and install. Temporary mechanical devices typically do not provide complete blockage resulting in a greater chance of conception. Permanent mechanical devices provide more reliable blockage, providing an almost complete prevention of conception, but are often difficult to install and expensive. Additionally, the installation is not reversible.

Thus, there is a need for a device for preventing conception that is easy to construct, easy to install, safe to use and that resists the occurrence of infection over an extended period of time.

It would be highly advantageous, therefore, to remedy the foregoing and other deficiencies inherent in the prior art.

Accordingly, it is an object of the present invention to provide a new and improved apparatus and methods for preventing fluid from passing into an oviduct of a female reproductive system.

Another object of the invention is to provide apparatus for preventing fluid transfer through an opening connecting an oviduct to a uterine cavity.

And another object of the invention is to provide apparatus for preventing fluid transfer through an opening connecting an oviduct to a uterine cavity which is extremely effective and can be reversed.

SUMMARY OF THE INVENTION

The above problems and others are at least partially solved and the above purposes and others realized in new and improved apparatus for preventing fluid transfer through an opening connecting an oviduct to a uterine cavity. The apparatus includes a body having a base with a periphery and a seal carried by the body for overlying and engaging uterine tissue leading to the opening. The seal receives fibroblast in-growth to create a hermetic seal between the oviduct and the uterine cavity. A peripheral anchor portion extends from the base for securing the body to the uterine tissue leading to the opening, the base overlying the opening.

The peripheral anchor may include a plurality of spikes extending from the periphery of the base. The spikes can terminate in a tissue engaging structure such as barbs. The peripheral anchor portion can also include a plurality of helical blades extending radially outwardly from the base. The helical blades can be carried by a blade disk coupled to the base or be integral with the base. The body supports an engaging member that may be rigidly grasp by a tool and which allows the apparatus to be manipulated during installation.

Consistent with the foregoing, associated methods of preventing fluid transfer through an opening connecting an oviduct to a uterine cavity may also be provided.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which:

FIG. 4 is a view showing the apparatus of FIG. 1 as it would appear being installed;

FIG. 5 is a view showing the apparatus as it would appear installed with a female reproductive system for preventing fluid transfer between an oviduct and a uterine cavity;

FIG. 6 is a perspective view of another embodiment of apparatus for preventing fluid transfer between an oviduct and a uterine cavity of a female reproductive system;

FIG. 7 is a side view of the apparatus of FIG. 6; and

FIG. 8 is an end view of the apparatus of FIG. 6 with the seal removed.

DETAILED DESCRIPTION OF A PREFERRED EMBODIMENT

Figure 1:
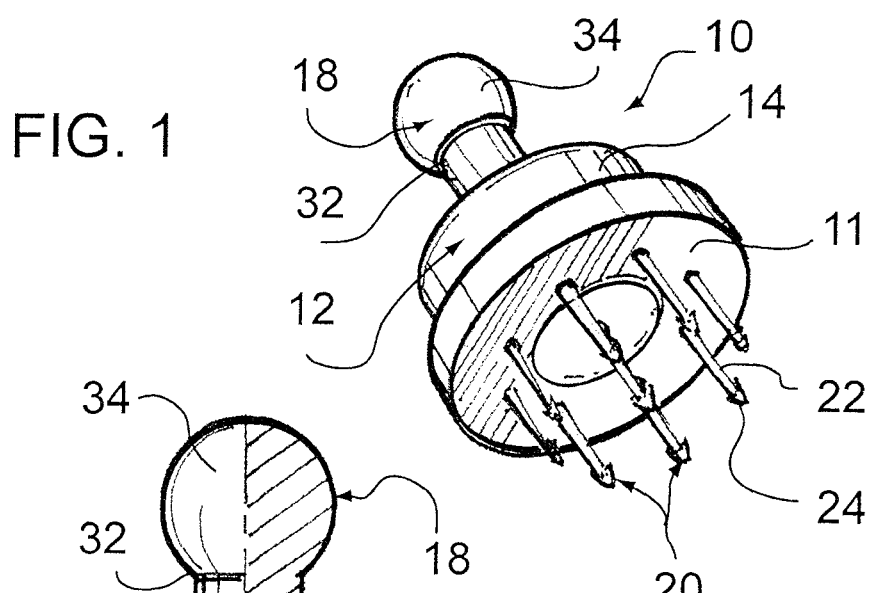
FIG. 1 is a perspective view of apparatus for preventing fluid transfer between an oviduct and a uterine cavity of a female reproductive system.
Figure 2:
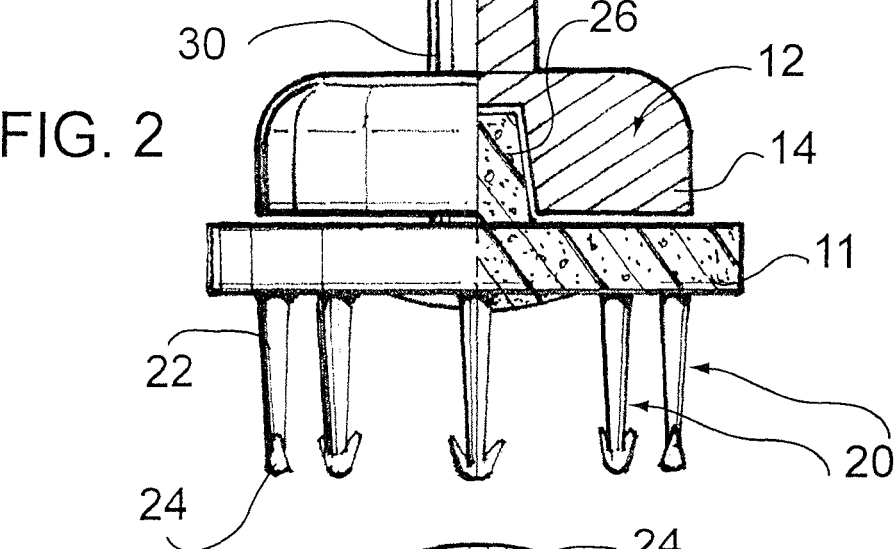
FIG. 2 is a partial sectional side view of the apparatus of FIG. 1.
Figure 3:
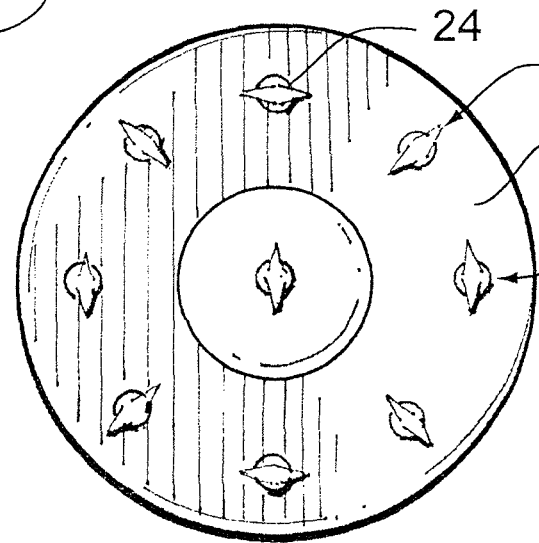
FIG. 3 is an end view of the apparatus of FIG. 1.

Turning now to the drawings, in which like reference characters indicate corresponding elements throughout the several views, attention is first directed to FIG. 1 illustrating a perspective view of apparatus 10 for preventing fluid transfer between an oviduct and a uterine cavity of a female reproductive system. Apparatus 10 includes a stop or seal 11 supported by a body 12. As can be seen in this embodiment, seal 11 has a circular disk shape and body 12 includes a circular base 14. It will be understood that while a circle is the preferred shape, other shapes, such as a square, an octagonal, etc., can be used. Referring also to FIGS. 2 and 3, body 12 is constructed of rigid, non-porous, bio-compatible material such as stainless steel, titanium, ceramics or a poly-base material. Body 12, or portions thereof, can also be formed of a biodegradable compound which will dissolve and be absorbed by the body over a period of time. The material is absorbed, flushed or eliminated by the human body over a certain period of time after installation. The biodegradable material may be any suitable material such as any one or more of a variety of biodegradable polymers such as polyglycolide and polylactide, and copolymers of glycolide and lactide, trimethylene carbonate, and caprolactone and the like. In this instance, only seal 11 will remain, or various portion of the body may remain if not formed of absorbable material. Body 12 includes a peripheral anchor portion which holds body 12 and seal 11 in position on the uterine wall as will be described presently, and an extension portion 18.

The peripheral anchor portion, in this embodiment, includes a plurality of spikes 20 extending perpendicularly from the periphery of base 14 of body 12, and passing through seal 11. While spikes 20 pass through seal 11 in this embodiment, it will be understood that the diameter of seal 11 may fit within the circle of spikes 20. Each of spikes 20 includes a shaft 22 terminating in a tissue engaging structure. In this embodiment, the tissue engaging structure is a barbed head 24. One skilled in the art will understand that other engagement structures can be employed. For example, one or more barbs may be employed, or the tissue engagement structure can be a conical enlargement. The enlargement leads with a point or vertex, and trails with a base or directrix that defines a step angle with shaft 22. The directrix defines a diameter greater than the outer diameter of shaft 22.

Seal 11 is a disk of material coupled to base 14 by a fastener, such as adhesives or a central plug 26 received within a socket of body 12 as in the present embodiment. Seal 11 may also a continuous annular body having a central opening fitting around a projection from base 14, or attached by a fastener such as a rivet, screws, spikes or the like. Seal 11 is preferably fabricated of a somewhat or highly deformable, porous material. In a preferred embodiment, body 20 is constructed of polytetrafluoroethylene (PTFE) plastic which, is a well known material sold under the trademark TEFLON. Appropriate porous PTFE materials are commercially available and may be produced by the process described in Japanese Patent Publication No. 135,60/67 and U.S. Pat. No. 3,953,566, which are incorporated by reference herein. Other acceptable porous materials manufactured and sold under the trademarks PROPLAST, DACRON or GORTEX may also be used for seal 11. Included in a list of preferred materials for seal 11 is cotton, polypropylene or silk mesh. Seal 11 defines micro porous fibrous structure consisting of small fibers and nodes connected together. Similar expanded PTFE products are presently in use for vascular prostheses and typically include pore sizes on the order of two microns or greater. Typical pore size for most effective utilization in vascular prostheses generally falls within the range of between approximately five to ten microns.

Regarding FIGS. 1 and 2, body 12 includes extension 18 that extends from base 14 away from spikes 20. In a preferred embodiment, extension 18 includes an inner end 30, an outer end 32 and an engaging member 34 positioned, in this specific embodiment, at or adjacent outer end 32. Engaging member 34 is intended to be substantially any structure allowing gripping by an insertion tool. Member 34 can be a ball joint, a ball joint with flat portion to allow rigid gripping or various other shapes such as cuboidal, hexagonal and the like.

Turning now to FIGS. 4 and 5, shown is an utero-tubal junction of a female reproductive system including a uterine cavity wall 40, and an opening 42 leading to an isthmus of an oviduct. To install apparatus 10, a guide catheter may be maneuvered into the uterine cavity by way of the vagina and the cervix. The catheter is preferably flexible which allows it to be easily maneuvered into the uterine cavity. The catheter preferably includes the operating channel of a hysteroscope, which is a commercially available device used primarily by gynecologists for examining and operating on the female reproductive system. A typical hysteroscope typically includes three parallel oriented channels that run longitudinally along a given length of the device. One of these channels provides a source of illumination, and second channel includes a fiberoptic bundle that provides illumination. The third channel can house a flexible guide having flexible jaws or tongs that can engage engaging member 34. The guide includes a mechanism that a physician may operate for moving the tongs between an open condition and a closed condition for engaging ball joint 34. By maneuvering the guide through the catheter, apparatus 10 can be positioned, with spikes 20 of the anchor portion surrounding opening 42. The spikes are then embedded in the tissue surrounding opening 42 as shown in FIG. 5. Engaging member 34 permits apparatus 10 to be securely held and articulated as needed relative to the placement device for providing a natural and easy alignment and anchoring of body 12 overlying opening 42. The fiberoptic bundle and the illuminating ability of the catheter allow the physician to visually identify opening 42.

With spikes 20 facing opening 42, shafts 22 may be easily inserted into the tissue around opening 42. Barbs 24 provide for a smooth insertion into the tissue, and provide an anchor holding apparatus 10 in position. When properly positioned, outer edges of seal 11 overlie and rest against the surface of uterine tissue leading to and defining opening 42 as shown in FIG. 5. Body 12 maintains a desired alignment between seal 11 and the uterine tissue leading to and defining opening 42. Once body 12 is anchored with seal 11 positioned against the uterine tissue leading to and defining opening 42, fibroblast in-growth between that surrounding uterine tissue and seal 11 commences immediately to form an initially weak but progressively stronger bond between seal 11 and the uterine tissue. Body 12 cannot be easily moved out of position due to the influence of the anchor portion. Spikes 20 firmly hold body 12 over opening 42, preventing apparatus 10 from inadvertently falling away from the oviduct. Thus, the anchor portion holds body 12 in position so that seal 11 can accept immediate fibroblast in-growth to provide a hermetic seal and fluid isolation between the oviduct and uterine cavity.

Apparatus 10 may be removed, even after fibroblast in-growth is complete, by grasping engaging member 34, such as with tongs, and forcibly removing apparatus 10. Because uterine and oviduct tissue is very resilient, tissue damage caused by the forcible removable of apparatus 10 heals very quickly.

Referring now to FIGS. 6, 7 and 8, another embodiment of apparatus for preventing fluid transfer between an oviduct and a uterine cavity of a female reproductive system, generally designated 50, is illustrated. Apparatus 50 is substantially identical to apparatus 10 in structure and function, and includes substantially the same elements. Accordingly, the reference characters used to describe apparatus 10 will also be used to describe apparatus 50, but only to the extent of their common structural components. For clarity, common reference characters used to describe apparatus 50 will include a prime ("'") symbol. In this regard, apparatus 50 includes seal 11' and body 12'. Body 12' includes a base 14', a peripheral anchor portion and an extension portion 18'. Rather than providing a plurality of spikes as in apparatus 10, the peripheral anchor of apparatus 50 includes a helical blade disk 52 having a pair of opposing helical blades 53 and 54 extending therefrom. Blade disk 52 is fastened securely and rigidly to base 14' by fasteners such as rivets screws, adhesives, etc. It will be understood that while a blade disk 52 is coupled to base 14' in the preferred embodiment, the blades can be formed integrally with body 12' and extend from base 14'.

In use, apparatus 50 is positioned over an opening 42 of an oviduct employing, for example, a device as described previously for apparatus 10. When positioned with seal 11' overlying opening 42, apparatus 10 is rotated causing blades 53 and 54 to enter the uterine wall. The helical shape causes blades 53 and 54 to pull body 12' and seal 11' firmly against the uterine wall overlying opening 42 and anchoring seal 11' in position. As a result, apparatus 50 cannot be easily moved out of position. Like spikes 20, blade disk 52 cooperates as a peripheral anchor that holds body 12' in place so that seal 11' can accept immediate fibroblast in-growth to provide a hermetic seal and fluid isolation between the oviduct and the uterine cavity.

The present invention has been described above with reference to a preferred embodiment. However, those skilled in the art will recognize that changes and modifications may be made in the described embodiments without departing from the nature and scope of the present invention. For example, while apparatus 50 employs helical blades as the peripheral anchor they may be developed more in the form a screw threads. Thus, apparatus 50 could be threaded into tissue with a continuous helical blade in the form of screw threads instead of two or more blades. Various changes and modifications to the embodiment herein chosen for purposes of illustration will readily occur to those skilled in the art. To the extent that such modifications and variations do not depart from the spirit of the invention, they are intended to be included within the scope thereof which is assessed only by a fair interpretation of the following claims.

Having fully described the invention in such clear and concise terms as to enable those skilled in the art to understand and practice the same, the invention claimed is:

1. Apparatus for preventing fluid transfer through an opening connecting an oviduct to a uterine cavity, the apparatus comprising:
    a body having a base with a periphery;
    a seal carried by the body for overlying and engaging uterine tissue leading to the opening and receiving fibroblast ingrowth to create a hermetic seal between the oviduct and the uterine cavity; and
    a helical blade extending radially outwardly from the base, the helical blade is carried by a blade disk coupled to the base and is for engaging the uterine tissue leading to the opening and securing the body to the uterine tissue leading to the opening, the base overlying the opening.

2. Apparatus of claim 1, wherein the body supports an engaging member that is graspable by a tool and which allows the apparatus to be manipulated during installation.

3. Apparatus of claim 2, wherein the engaging member is carried by an extension of the body.

4. Apparatus of claim 1, wherein the seal is formed of a biocompatible material that stimulates in-growth of fibroblastic tissue.

5. Apparatus as claimed in claim 1, wherein the body is fabricated of a biodegradable material.

6. Apparatus for preventing fluid transfer through an opening connecting an oviduct to a uterine cavity, the apparatus comprising:
    a body;
    a seal coupled to the body for engaging uterine tissue surrounding and defining the opening, the seal formed of a biocompatible material that stimulates in growth of fibroblastic tissue to create a continuous hermetic seal; and
    a plurality of helical blades supported by the body, the helical blades are carried by a blade disk coupled to the body and are for entering the uterine tissue leading to the opening upon the application of a twisting movement of the body, engaging the uterine tissue and maintaining the seal in engagement to the uterine tissue surrounding and defining the opening, the seal overlying the opening.

7. Apparatus of claim 6, wherein the body supports an engaging member that is graspable by a tool and which allows the apparatus to be manipulated during installation.

8. Apparatus of claim 7, wherein the engaging member is carried by an extension of the body.

9. Apparatus as claimed in claim 6, wherein the body is fabricated of a biodegradable material.

* * * * *